US011763948B2

(12) United States Patent
Sughrue et al.

(10) Patent No.: US 11,763,948 B2
(45) Date of Patent: Sep. 19, 2023

(54) CENTRALITY RANKINGS OF NETWORK GRAPHS GENERATED USING CONNECTOMIC BRAIN DATA

(71) Applicant: Omniscient Neurotechnology Pty Limited, Sydney (AU)

(72) Inventors: Michael Edward Sughrue, Brighton le Sands (AU); Stephane Philippe Doyen, Mount Kuring Gai (AU); Peter James Nicholas, South Hurstville (AU); Hugh Monro Taylor, Point Piper (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 108 days.

(21) Appl. No.: 17/586,718

(22) Filed: Jan. 27, 2022

(65) Prior Publication Data

US 2022/0157461 A1     May 19, 2022

Related U.S. Application Data

(63) Continuation of application No. 17/066,196, filed on Oct. 8, 2020, now Pat. No. 11,264,137.

(51) Int. Cl.
*G16H 50/20*     (2018.01)
*G16H 50/50*     (2018.01)
(Continued)

(52) U.S. Cl.
CPC .............. *G16H 50/20* (2018.01); *A61B 5/055* (2013.01); *A61B 5/4088* (2013.01);
(Continued)

(58) Field of Classification Search
CPC ........ G16H 50/20; G16H 50/50; G16H 50/70; G16H 40/67; G16H 40/20; G16H 70/60;
(Continued)

(56) References Cited

U.S. PATENT DOCUMENTS 10,149,618 B1    12/2018   Tandon et al.
11,264,138 B1    3/2022   Sughrue et al.
(Continued)

OTHER PUBLICATIONS

Du et al., "Structural brain network measures are superior to vascular burden scores in predicting early cognitive impairment in post stroke patients with small vessel disease" Neuroimage Clin., 2018, 22:101712.
(Continued)

*Primary Examiner* — Michael Tomaszewski
(74) *Attorney, Agent, or Firm* — Fish & Richardson P.C.

(57) ABSTRACT

Methods, systems, and apparatus, including computer programs encoded on computer storage media, for generating a mental health prediction for a patient using a centrality ranking of the brain of the patient. One of the methods includes obtaining brain data of a patient, wherein the brain data comprises, for each of a plurality of pairs of parcellations formed from a set of parcellations where each pair comprises a first parcellation and a second parcellation, data characterizing a number of tracts connecting the first parcellation and the second parcellation; determining a network graph from the brain data; generating, for each of a plurality of nodes in the network graph, a measure of centrality of the node; determining a centrality ranking of the plurality of nodes of the network graph according to the respective measures of centrality; generating a mental health prediction for the patient using the determined centrality ranking.

21 Claims, 7 Drawing Sheets

(51) Int. Cl.

| | |
|---|---|
| *G16H 50/70* | (2018.01) |
| *G16H 40/20* | (2018.01) |
| *G16H 70/60* | (2018.01) |
| *G06F 16/901* | (2019.01) |
| *A61B 5/00* | (2006.01) |
| *A61B 5/055* | (2006.01) |
| *G16H 40/67* | (2018.01) |
| *G16H 20/10* | (2018.01) |
| *G16H 20/30* | (2018.01) |
| *G16H 20/40* | (2018.01) |
| *G16H 20/70* | (2018.01) |

(52) U.S. Cl.
CPC .......... *A61B 5/4848* (2013.01); *A61B 5/7264* (2013.01); *A61B 5/7275* (2013.01); *A61B 5/742* (2013.01); *G06F 16/9024* (2019.01); *G16H 40/20* (2018.01); *G16H 40/67* (2018.01); *G16H 50/50* (2018.01); *G16H 50/70* (2018.01); *G16H 70/60* (2018.01); *A61B 5/002* (2013.01); *G16H 20/10* (2018.01); *G16H 20/30* (2018.01); *G16H 20/40* (2018.01); *G16H 20/70* (2018.01)

(58) Field of Classification Search
CPC ........ G16H 20/40; G16H 20/30; G16H 20/10; G16H 20/70; G06F 16/9024; A61B 5/055; A61B 5/4088; A61B 5/4848; A61B 5/7264; A61B 5/7275; A61B 5/742; A61B 5/002
See application file for complete search history.

(56) References Cited

U.S. PATENT DOCUMENTS

| | | | |
|---|---|---|---|
| 2011/0295515 A1 | 12/2011 | Grady et al. | |
| 2013/0231552 A1 | 9/2013 | Grady et al. | |
| 2015/0018664 A1* | 1/2015 | Pereira | G16H 50/20 600/410 |
| 2015/0164431 A1 | 6/2015 | Terry et al. | |
| 2015/0272468 A1* | 10/2015 | Liu | A61B 5/0042 600/410 |
| 2016/0284082 A1 | 9/2016 | Varkuti | |
| 2016/0300352 A1* | 10/2016 | Raj | G06V 10/764 |
| 2017/0035320 A1 | 2/2017 | Verma et al. | |
| 2018/0368720 A1 | 12/2018 | Lee et al. | |
| 2019/0272889 A1 | 9/2019 | Murray et al. | |
| 2020/0043615 A1* | 2/2020 | Reimann | G16H 50/30 |
| 2020/0225308 A1 | 7/2020 | Dosenbach et al. | |
| 2020/0230413 A1 | 7/2020 | Madhavan et al. | |
| 2020/0288980 A1* | 9/2020 | Stern | G16H 50/70 |
| 2022/0148738 A1 | 5/2022 | Sughrue et al. | |

OTHER PUBLICATIONS

Goubran et al., "Multimodal image registration and connectivity analysis for integration of connectomic data from microscopy to MRI" Nature Comm., Dec. 2019, 10(1):1-7.

International Search Report and Written Opinion in International Appln. No. PCT/AU2021/051168, dated Jan. 20, 2022, 7 pages.

Medium.com [online], "A Simple Guide to Scikit-learn Pipelines", Feb. 2019, retrieved on Oct. 19, 2020, retrieved from URL <https://medium.com/vickdata/a-simple-guide-to-scikit-learn-pipelines-4ac0d974bdcf>, 6 pages.

* cited by examiner

CENTRALITY RANKINGS OF NETWORK GRAPHS GENERATED USING CONNECTOMIC BRAIN DATA

CROSS-REFERENCE TO RELATED APPLICATIONS

This application is a continuation of, and claims priority to, U.S. patent application Ser. No. 17/066,196, filed Oct. 8, 2020, the entire contents of which are incorporated herein by reference.

This application is related to U.S. patent application Ser. No. 17/066,186, filed Oct. 8, 2020, entitled "Generating Brain Network Impact Scores," to Michael Edward Sughrue, Stephane Philippe Doyen, Peter James Nicholas, and Bradley Allan Fernald, and incorporated herein by reference in its entirety.

BACKGROUND

This specification relates to processing data related to the brain of a patient, e.g., functional magnetic resonance imaging (MRI) data and/or tractography data.

Brain functional connectivity data characterizes, for each of one or more pairs of locations within the brain of a patient, the degree to which brain activity in the pair of locations is correlated.

One can process images of the brain of a patient, e.g., using magnetic resonance imaging (MRI), diffusion tensor imaging (DTI), or functional MRI imaging (fMRI). Diffusion tensor imaging uses magnetic resonance images to measure diffusion of water in a human brain. One can use the measured diffusion to generate tractography data, which can include images of neural tracts and corresponding white matter fibers of the subject brain.

Data related to the brain of a single patient can be highly complex and high-dimensional, and therefore difficult for a clinician to manually inspect and parse, e.g., to plan a surgery or categorize the patient for follow up regarding a brain disease or mental disorder. For example, a correlation matrix, e.g., a correlation matrix of fMRI data, of the brain of a patient can be a matrix with hundreds of thousands or millions of elements.

SUMMARY

This specification describes a system that is configured to process brain data of a patient and generate a mental health prediction for the patient. The system can represent the brain of the patient as a network, e.g., a network represented by a network graph, where each node in the network graph corresponds to a respective region of the brain and each edge between two nodes corresponding to respective regions characterizes a connection between the two regions. For example, each node in the graph can correspond to a parcellation of the brain, and each edge can correspond to one or more tracts of the brain connecting respective parcellations.

The system can determine a measure of centrality for each region of the brain represented by a respective node in the network graph. For example, the system can determine the PageRank of each node in the graph. The system can then rank the regions of the brain according to their respective measures of centrality to generate a respective centrality rank for each region of the brain.

In this specification, the ordering of the nodes of a network graph according to their measures of centrality is called a "centrality ranking," while the position of a node in the ranking of nodes by their measures of centrality is called the "centrality rank" of the node.

After the system generates the centrality ranks for each of one or more regions of the brain of the patient, the system can use the centrality ranks to determine a mental health prediction for the patient. The mental health prediction can include a determination of whether to perform a particular treatment on the brain of the patient, e.g., whether to administer a particular drug, whether to perform transcranial magnetic stimulation (TMS), or whether to perform a particular surgery. Instead or in addition, the mental health prediction can include a prediction of whether the patient has a particular brain disease, e.g., autism, schizophrenia, or depression. Instead or in addition, the mental health prediction can include a determination of degree of trauma that the particular region of the brain has experienced. Instead or in addition, the mental health prediction can include a measure of change in the health of the brain of the patient over time, e.g., a difference between a first set of centrality ranks generated from brain data captured at a first time point and a second set of centrality ranks generated from brain data captured at a second time point. Instead or in addition, the mental health prediction can include a prediction of a relationship between two or more different regions of the brain, e.g., a degree of correlation between respective centrality ranks of the different regions of the brain.

In this specification, brain data can be any data characterizing the brain of a patient. For example, brain data can include one or both of i) direct measurement data of the brain of the patient, e.g., images of the brain collected using brain imaging techniques, or ii) data that has been derived or generated from initial measurement data of the brain of the patient, e.g., correlation matrices.

Particular embodiments of the subject matter described in this specification can be implemented so as to realize one or more of the following advantages.

As discussed above, a set of brain data characterizing the brain of a single patient can often be incredibly large and complicated, and thus it can be difficult and time consuming for a user to extract useful information from the set of brain data. Using techniques described in this specification, a system can process brain data of a patient and automatically determine respective centrality ranks of one or more regions of the brain, which is a useful metric for the current health of the brain. A user can then use the determined centrality ranking to make clinical decisions about the treatment of the patient. Thus, the amount of time that a user must spend analyzing raw brain data to determine the health of the brain can be drastically reduced or even eliminated, resulting in improved outcomes for patients, users and/or clinicians, especially when effective care requires time sensitive investigations.

According to one or more embodiments described in this specification, users can use the centrality ranks of a particular region in the brain to standardize treatments across patients. As a particular example, medical professionals who are experts on a brain disease associated with the particular region of the brain can establish standards for care with reference to centrality rank benchmarks, e.g., these professionals can provide a first treatment (e.g., TMS) to a patient if the centrality rank meets a first criteria and provide a second treatment (e.g., brain surgery) to the patient if the centrality rank meets a second criteria.

Ranking the regions of the brain according to their respective measures of centrality can normalize the brain data of each individual patient. While the raw number of brain tracts in the brains of different patients can differ significantly, generally the centrality ranking of the regions of the brain is similar across patients. Therefore, patterns of brain data that are indicative of a brain condition can be identified in each individual patient with the brain condition, regardless of the raw quantity of brain tracts in the brain of the patient.

Ranking the regions of the brain according to their respective measures of centrality can normalize the brain data of a patient across time. Typically, as a patient grows older, the number of tracts in the brain of the patient naturally decreases, while the centrality ranking of the regions in the brain of the patient remain roughly the same. Therefore, patterns of brain data across time that are indicative of a brain condition can be identified in the patient, regardless of the current age of the patient and any age-related reduction in the number of tracts not related to the brain condition.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes a system that can process brain data of a patient to generate a mental health prediction for the patient.

Figure 1A:
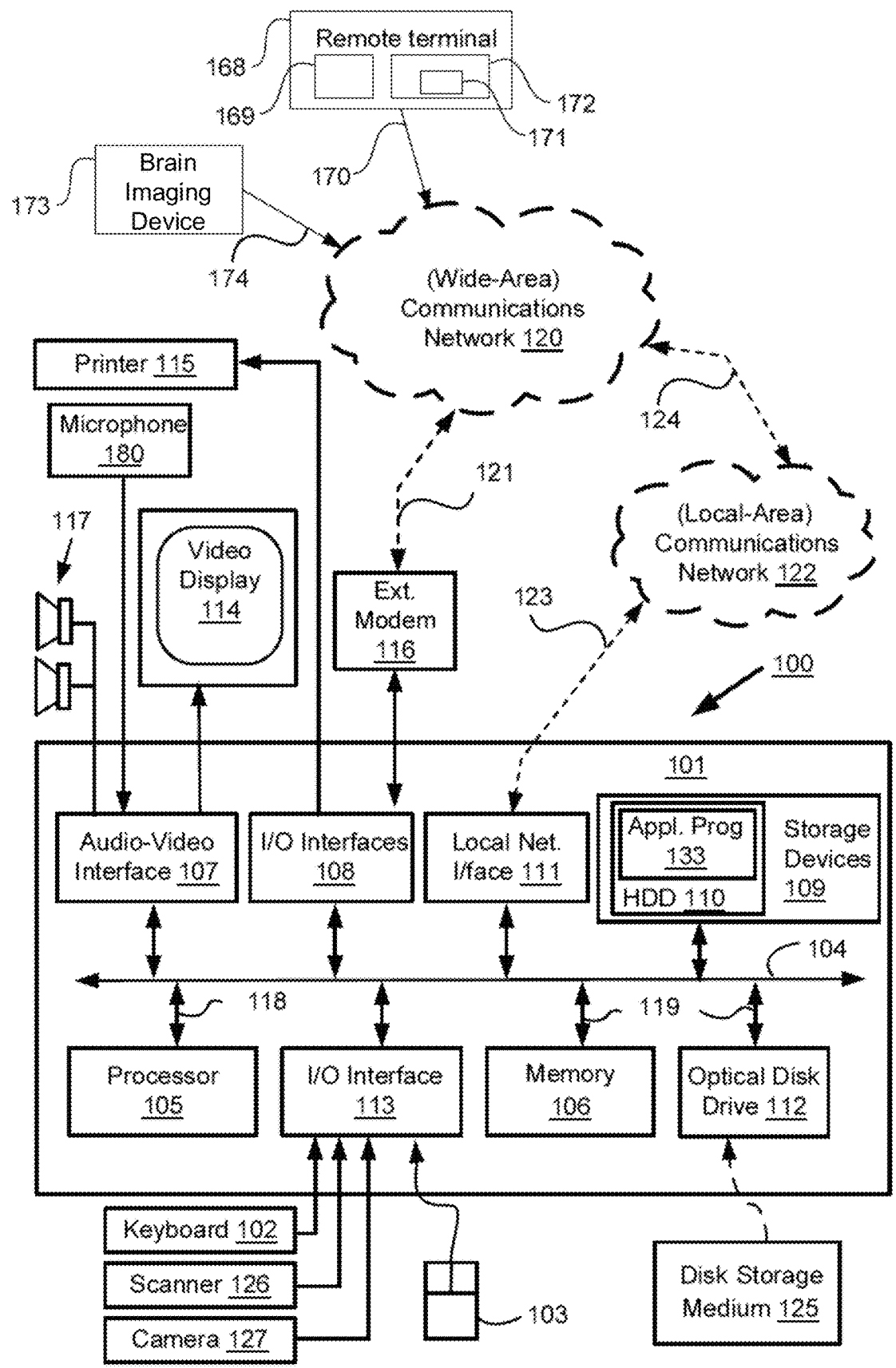
FIG. 1A and FIG. 1B are block diagrams that illustrate an example computer system for use in processing medical images.
Figure 1B:
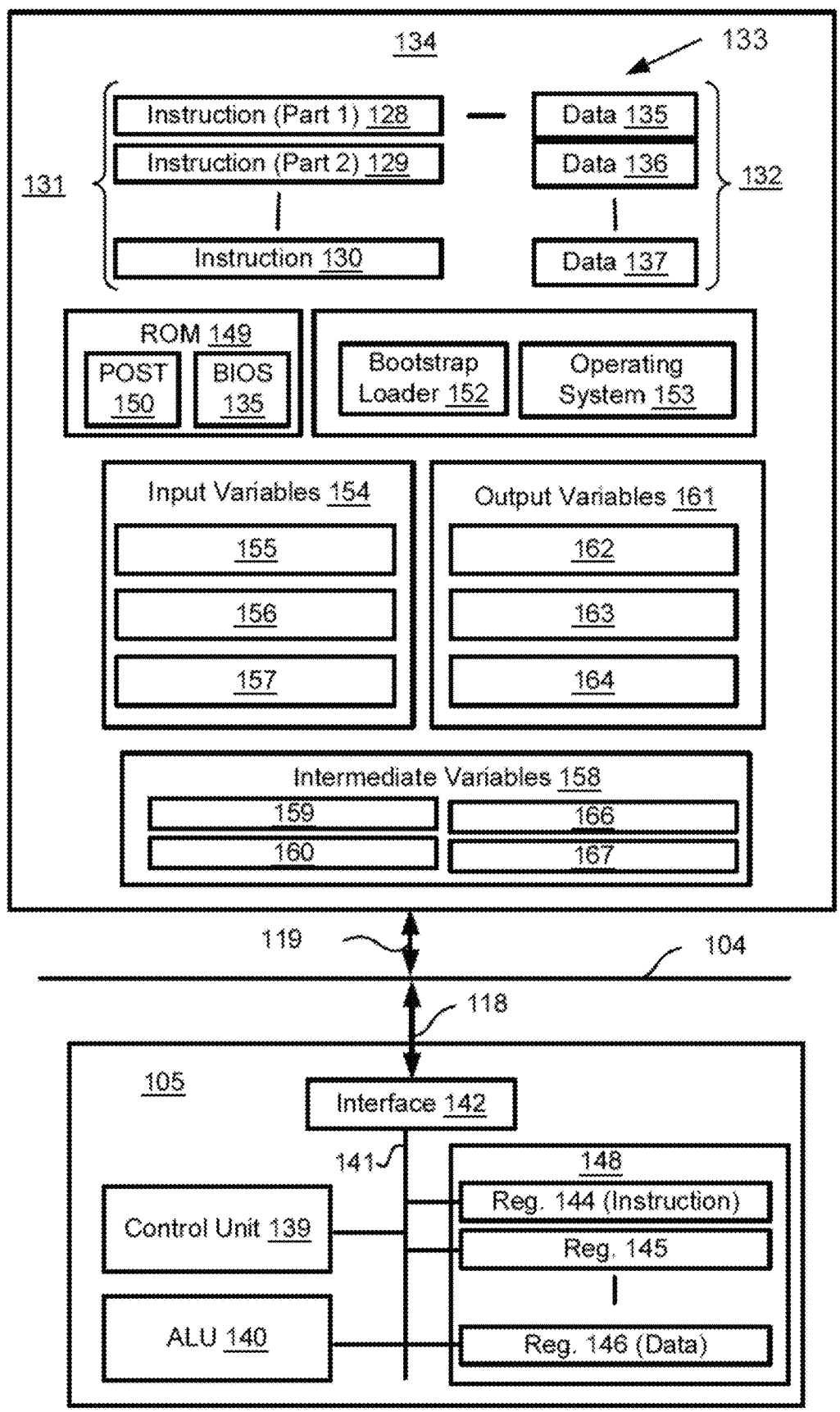

FIGS. 1A and 1B are block diagrams of a general-purpose computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101.

The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a brain imaging device 173 such such as an Mill or DTI scanner, across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing the brain of a patient, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2A:
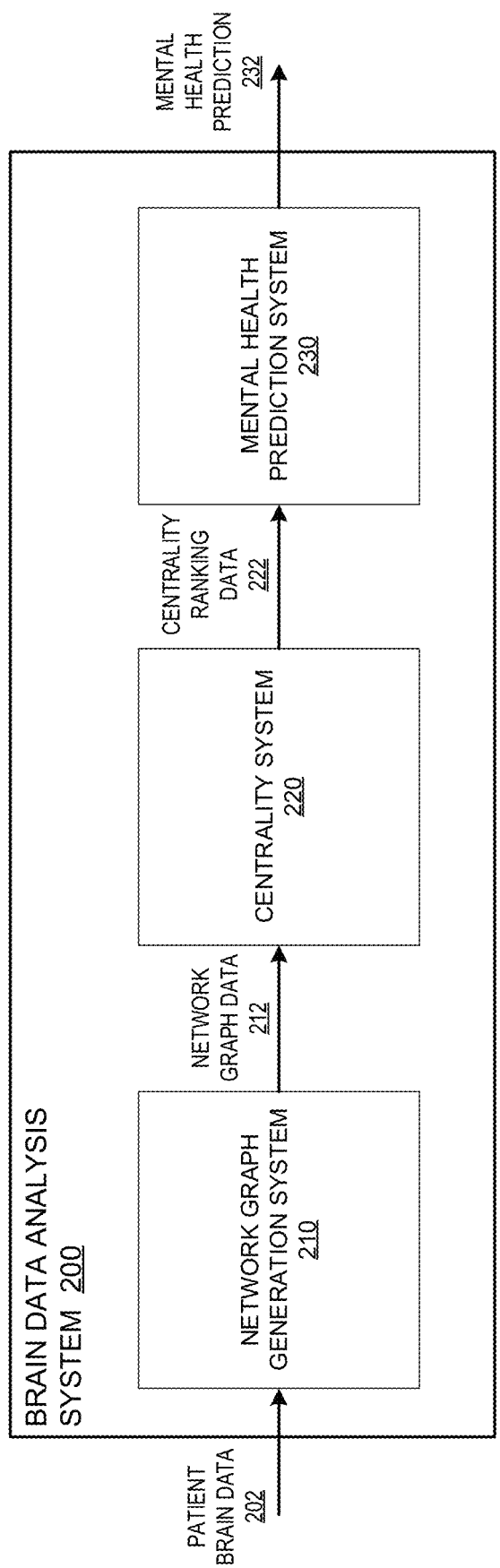
FIG. 2A is a diagram of an example brain data analysis system.

FIG. 2A is a diagram of an example brain data analysis system 200. The brain data analysis system 200 is an example of a system implemented as computer programs on one or more computers in one or more locations, in which the systems, components, and techniques described below can be implemented.

The brain data analysis system 200 is configured to obtain patient brain data 202 characterizing the brain of a patient and process the patient brain data 202 to generate a mental health prediction 232 characterizing the health of the brain of the patient. The brain data analysis system 200 includes a network graph generation system 210, a centrality system 220, and a mental health prediction system 230.

In some implementations, the patient brain data 202 includes brain tractography data that identifies, for each pair of two parcellations in a set of parcellations in the brain of the patient, a number of tracts connecting the two parcellations. In some such implementations, the tractography data can be normalized. For example, the number of tracts between each pair of parcellations can be normalized according to the largest number of tracts connecting a respective pair of parcellations in the brain of the patient, or according to the total number of tracts in the brain of the patient.

The set of parcellations can be defined by a brain atlas. In this specification, a brain atlas is data that defines one or more parcellations of a brain of a patient, e.g., by defining in a common three-dimensional coordinate system the coordinates of the outline of the parcellation or the volume of the parcellation.

Instead or in addition, the patient brain data 202 can include data characterizing a health of the tracts connecting respective pairs of parcellations in the brain of the patient. As a particular example, the patient brain data 202 can include fractional anisotropy data that characterizes, for each pair of parcellations in the brain of the patient that share at least one tract, a health of the tracts connecting the pair of parcellations. As another particular example, the patient brain data 202 can include correlation data that characterizes, for each pair of parcellations in the brain of the patient, a degree of correlation between the brain activity of the pair of parcellations. For instance, the patient brain data 202 can include a correlation matrix that includes a respective row and column for each parcellation, where the value of each element is the degree of correlation between the parcellation corresponding to the row and the parcellation corresponding to the column.

In some cases, the number of tracts or the health of the tracts in the brain of the patient identified in the brain data 202 can depend on the particular device used to capture the brain tractography data and/or the time or location at which the tractography data was captured. That is, in this specification "a number of tracts" refers to the number of tracts identified in a particular set of brain data 202 captured by a respective machine at a respective time point.

The network graph generation system 210 is configured to receive the patient brain data 202 and to generate network graph data 212 according to the patient brain data 202. The network graph data 212 defines a network graph that characterizes the brain of the patient. For example, each node in the network graph can correspond to a respective region of the brain of the patient, e.g., a respective parcellation.

Each edge between a pair of nodes in the network graph can characterize a connection between the pair of nodes. For example, the network graph can include an edge between a first node and a second node if there exists one or more tracts connecting the parcellation corresponding to the first node and the parcellation corresponding to the second node, according to the patient brain data 202. In some implementations, the edge between a first node and a second node can be weighted according to a number of tracts connecting the corresponding parcellations; that is, a higher edge weight indicates a larger number of tracts connecting the corresponding parcellations. Instead or in addition, the edge between a first node and a second node can be weighted according to the health of the tracts connecting the corresponding parcellations; that is, a higher edge weight indicates better health of the tracts connecting the corresponding parcellations.

Exemplary network graphs are described in more detail below with respect to FIG. 3.

In some implementations, the network graph data 212 can be defined by an adjacency matrix. For example, the adjacency matrix can include a respective row and a respective column for each node in the network graph, where the element in a particular row and column defines the edge between the node corresponding to the row and the node corresponding to the column. If the network graph is an unweighted graph, the adjacency matrix can include elements that have value 0 or 1, where value 0 indicates that there is no edge between the corresponding nodes and value 1 indicates that there is an edge between the corresponding nodes. If the network graph is a weighted graph, the value of each element can define the weight of the edge between the corresponding nodes.

The centrality system 220 is configured to receive the network graph data 212 and to process the network graph data 212 to generate centrality ranking data 222 that includes a ranking of each of the nodes of the network graph according to a measure of centrality. The measure of centrality of a node in the network graph characterizes a level of "importance" of the node within the network graph. Typically, a first node that has more edges and higher edge weights has a higher measure of centrality than a second node that has fewer edges and lower edge weights.

As particular examples, the centrality data 222 can include a respective ranking of the nodes of the network graph according to one or more of: a PageRank of the node, the degree of the node (which measures the number of edges incident to the node), the strength of the node (which measures the sum of the edges incident to the node), the betweenness of the node (which measures the number of shortest paths between respective pairs of nodes in the graph that pass through the node), or the closeness of the node (which measures the reciprocal of the sum of the lengths of the shortest paths between the node and each other node in the graph).

In some implementations, the measures of centrality of respective nodes in the network graph can be normalized. For example, the measures of centrality can be normalized within the patient, e.g., according to the largest measure of centrality in the network graph or according to the sum of all measures of centrality in the network graph. As another example, the measures of centrality can be normalized across subjects, e.g., using multiple network graphs corresponding to respective different patients.

Using the centrality ranking of the nodes, instead or in addition to the raw measures of centrality of the nodes, to generate health predictions 232 can be useful because centrality ranks can serve to normalize the total number of brain tracts across all patients. In other words, centrality ranks are less sensitive to variation in the number of brain tracts across patients.

For example, a first patient may naturally have significantly more brain tracts than a second patient, e.g., 2×, 5×, or 10× more brain tracts, while the health of the respective brains of the patients is roughly the same. In these cases, using the raw measures of centrality of the nodes in the network graph (corresponding to parcellations in the brain) to generate mental health predictions 232 may incorrectly indicate that the brain of the first patient is significantly healthier than the brain of the second patient. Using the centrality ranks of the nodes, which are usually largely consistent across patients, instead of, or in addition to, the raw measures of centrality can normalize the mental health predictions 232 for differences in the raw number of tracts in the brains of patients.

As another example, typically as a patient grows older the number tracts in the brain of the patient decreases, while the centrality ranks of the parcellations in the brain of the patient remain roughly the same. If the brain of the aging patient is otherwise healthy, then a user of the brain data analysis system 200 might prefer that the mental health prediction 232 for the patient not indicate that the brain of the patient is unhealthy. Thus, using centrality ranks can cause the mental health prediction 232 of a patient to vary less as the patient ages just based on typical age-related reduction in the number of tracts not related to brain disease.

Conversely, some brain diseases, e.g., Alzheimer's or dementia, can cause particular parcellations in the brain of a patient to decay more quickly than other parcellations. In these cases, both the raw measures of centrality and the centrality ranks of the nodes corresponding to the particular parcellations affected by the disease will decrease as the disease progresses. Thus, the mental health prediction 232 for the patient can correctly indicate an issue with the particular parcellations.

In some implementations, in addition to the respective centrality rank of each node in the network graph, the centrality ranking data 222 also includes the raw measures of centrality corresponding to each node in the network graph.

The mental health prediction system 230 is configured to receive the centrality data 222 from the centrality system 220 and to generate the mental health prediction 232.

In this specification, a mental health prediction of a user can be a prediction regarding any aspect of the mental health status of the user. For example, a mental health prediction can represent the likelihood that the user has one or more brain diseases. As another example, the mental health prediction can represent a likelihood that the user will develop one or more brain diseases or traits in the future, e.g., a likelihood that the user will develop a particular addiction. Mental health predictions are discussed in more detail below with respect to FIG. 5.

The mental health prediction system 230 can process the centrality ranking data 222 to generate the mental health prediction 232, and then provide the mental health prediction to one or more downstream systems.

For example, the mental health prediction system 230 can provide the mental health prediction 232 to a graphical user interface that displays data characterizing the mental health prediction 232 to a user. As a particular example, the mental health prediction 232 can include an identification of one or more parcellations whose centrality rank is determined by the mental health prediction system 230 to be anomalous, i.e., different than the typical centrality rank of the parcellation. In this example, the graphical user interface can display data to the user identifying the one or more anomalous parcellations. The graphical user interface can also display data identifying one or more brain diseases that are associated with the one or more identified parcellations.

An example mental health prediction system is described in more detail below with respect to FIG. 2B.

Figure 2B:
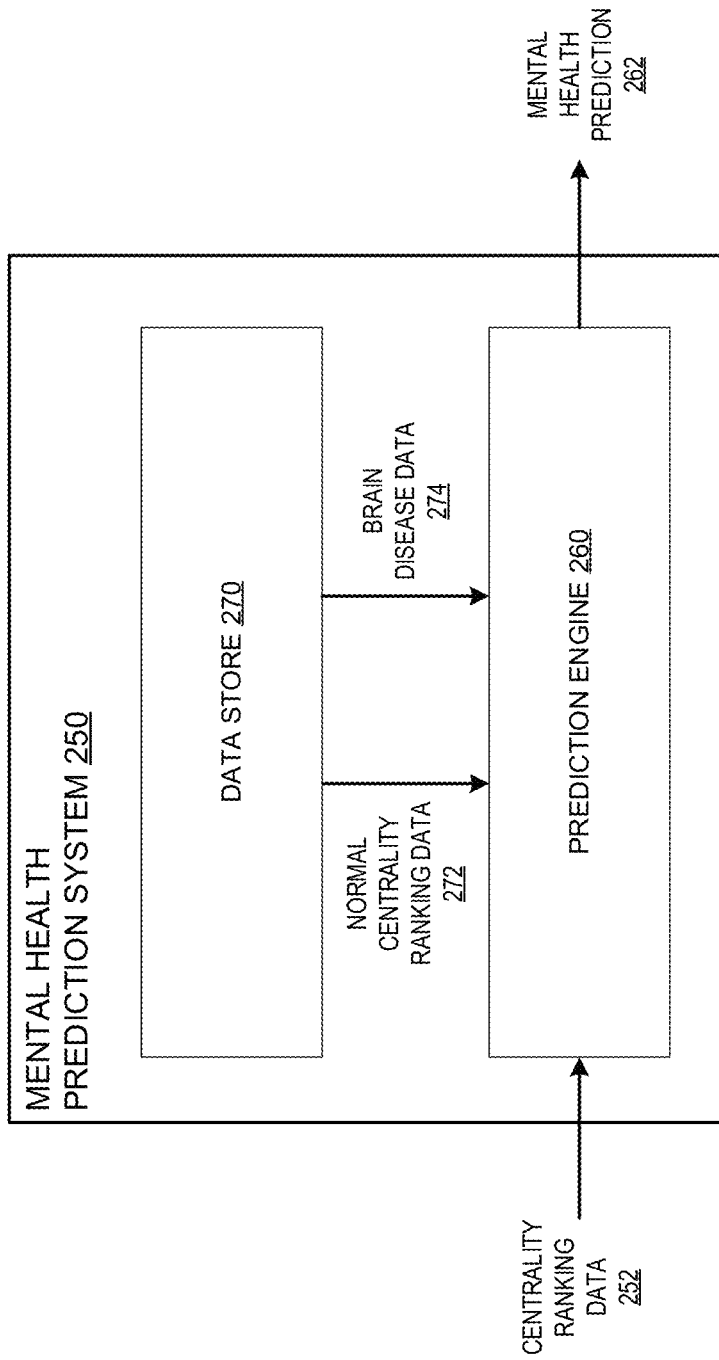
FIG. 2B is a diagram of an example mental health prediction system.

FIG. 2B is a diagram of an example mental health prediction system 250. The mental health prediction system 250 is an example of a system implemented as computer programs on one or more computers in one or more locations, in which the systems, components, and techniques described below can be implemented.

The mental health prediction system 250 includes a prediction engine 260 that is configured to receive centrality ranking data 252 that identifies, for each of multiple regions in the brain of a patient, a centrality rank of the region. For example, the centrality ranking data 252 can include a respective centrality rank for each parcellation in a set of parcellations in the brain of the patient. The prediction engine 260 processes the centrality ranking data 252 to generate a mental health prediction 262 that characterizes the health of the brain of the patient.

In some implementations, the prediction engine 260 obtains normal centrality ranking data 272 from a data store 270. The normal centrality ranking data 272 can identify, for each region in the brain of the patient, respective centrality ranks that are considered "normal." For example, the normal centrality ranking data 272 can include a mean or median centrality rank for each region of the brain. As another example, the normal centrality ranking data 272 can include a range of centrality ranks for each region of the brain, e.g., a range of 2, 5, 10, or 20 centrality ranks. The normal centrality ranking data 272 can be determined using the brain data of multiple respective other patients. As a particular example, the normal centrality ranking data 272 can be determined from brain data captured from hundreds, thousands, or millions of other patients.

The prediction engine 260 can compare the centrality ranking data 252 for the patient and the normal centrality ranking data 272 to generate the mental health prediction 262. For example, the prediction generation engine 260 might identify one or more regions of the brain whose centrality rank in the centrality ranking data 252 is outside of the range of normal centrality ranks identified in the normal centrality ranking data 272. The prediction engine 260 can identify the one or more regions in the mental health prediction 262. In some implementations, the prediction engine 260 obtains brain disease data 274 from the data store 270. The brain disease data 274 can identify one or more regions of the brain that are associated with respective brain diseases. The brain disease data 274 can be determined using the brain data of multiple respective other patients. For example, a system can generate centrality ranking data for each of multiple patients who have a disease. The system might then observe that the generated centrality ranks of one or more particular regions are consistently different than the corresponding centrality ranks of patients who do not have the disease, e.g., consistently outside of a range defined by the normal centrality ranking data 272. The system can then determine that the one or more regions are associated with the disease.

As a particular example, the prediction engine 260 can identify one or more regions of the brain that both i) have a centrality rank in the centrality ranking data 252 that is outside of the range of normal centrality ranks identified in the normal centrality ranking data 272 and ii) are associated with a respective brain diseases in the brain disease data 274. The prediction engine 260 can identify the one or more regions of the brain and the one or more respective brain diseases in the mental health prediction 262.

As another particular example, the brain disease data 274 can identify multiple regions of the brain that are collectively associated with a particular brain disease, where if brain data corresponding to each of the multiple regions is abnormal then that indicates that the patient might have the particular brain disease. In this example, the prediction engine 260 can determine, for each of the multiple regions of the brain, whether the centrality rank of the region in the centrality ranking data 252 is outside of the range of normal centrality ranks identified in the normal centrality ranking data 274. If each of the multiple regions have abnormal centrality ranks, then the prediction engine 260 can identify in the mental health prediction 262 the multiple regions and the particular brain disease that typically has the same or similar multiple centrality rank changes.

In some implementations, the brain disease data 274 can identify, for each region of the brain associated with a particular brain disease, a range of centrality ranks for the region that might indicate that the patient has the particular brain disease. The range of centrality ranks can be determined using the brain data of multiple respective other patients. For example, a system can generate centrality ranking data for each of multiple patients who have the particular disease. The system might then observe that the generated centrality ranks of one or more particular regions are consistently within a respective particular range while the corresponding centrality ranks of patients who do not have the particular disease are consistently outside the particular range. The system can then determine that the particular disease is associated with the particular ranges of the respective centrality ranks of the one or more particular regions.

For example, the prediction engine 260 can identify one or more regions of the brain whose centrality rank in the centrality ranking data 252 is within the range of centrality ranks associated with a respective brain disease in the brain disease data 274. The prediction engine 260 can identify the one or more regions of the brain and the one or more respective brain diseases in the mental health prediction 262.

As another particular example, the brain disease data 274 can identify multiple regions of the brain that are collectively associated with a particular brain disease, where the centrality rank of each of the multiple regions must be within a respective range to indicate that the patient might have the particular brain disease. In this example, the prediction engine 260 can determine, for each of the multiple regions of the brain, whether the centrality rank of the region in the centrality ranking data 252 is within the range of centrality ranks associated with the particular brain disease in the brain disease data 274. If each of the multiple regions have centrality ranks within the respective range, then the prediction engine 260 can identify the multiple regions and the particular brain disease in the mental health prediction 262.

In some implementations, the prediction engine 260 receives multiple sets of centrality ranking data 252 of the patient, where each set of centrality ranking data 252 corresponds to a respective different time point. That is, each set of centrality ranking data 252 is generated from brain data that was captured at a respective different time point.

For example, the prediction engine 260 can compare the multiple sets of centrality ranking data 252 and identify one or more regions of the brain whose centrality ranks changes across the multiple sets of centrality ranking data 252. As a particular example, the prediction engine 260 can identify each region of the brain whose centrality rank changes by at least a threshold amount across the multiple sets of centrality ranking data 252, e.g., whose ranking changed by 5, 10, or 20 positions. The prediction engine 260 can include the one or more identified regions of the brain in the mental health prediction 262.

In some implementations, each region can have a different threshold for changes in its centrality rank that are to be identified by the prediction engine 260. For example, the normal centrality ranking data 272 can identify, for each region in the brain of the patient, a number of positions that the centrality rank can change before the prediction engine 260 should identify the region in the mental health prediction 262. In some such implementations, each region has a different threshold for increases in its centrality rank and for decreases in its centrality rank. As a particular example, the normal centrality ranking data 272 might identify one or more parcellations in the brain step of the patient for which a decrease in the centrality rank of the parcellations by more than a few positions might indicate an issue with the brain of the patient.

As another example, the prediction engine 260 can identify one or more regions of the brain that both i) have a centrality rank that changes across the multiples sets of centrality ranking data 252 by at least the threshold amount corresponding to the region and ii) are associated with a respective brain diseases in the brain disease data 274. The prediction engine 260 can identify the one or more regions of the brain and the one or more respective brain diseases in the mental health prediction 262.

In some implementations, the brain disease data 274 can identify, for each region of the brain associated with a particular disease, a particular change or a range of changes of the centrality rank for the region across time that might indicate that the patient has the particular disease. The particular change or range of changes of the centrality ranks across time can be determined using the brain data of multiple respective other patients. For example, a system can generate multiple sets of centrality ranking data at respective different time points for each of multiple patients who have the particular disease. The system might then observe that the generated centrality ranks of one or more particular regions consistently change by the same number of positions or range of numbers of positions across time while the corresponding centrality ranks of patients who do not have the disease do not change in the same way. The system can then determine that the disease is associated with the particular change or range of changes of the centrality ranks of the one or more respective particular regions, and provide data characterizing the associated to the data store 270.

For example, the prediction engine 260 can identify one or more regions of the brain whose centrality ranks in the multiple sets of centrality ranking data 252 change across time by the number of positions or within the range of numbers of positions associated with a respective brain disease in the brain disease data 274. The prediction engine 260 can identify the one or more regions of the brain and the one or more respective brain diseases in the mental health prediction 262.

In some such implementations, the brain disease data 274 can identify different stages of a particular brain disease, where each stage is associated with a different change in the centrality ranks of respective particular regions of the brain. The prediction engine 260 can then identify that the centrality ranks of the particular regions change across the multiple sets of centrality ranking data 252 in the way that is identified in the brain disease data 274 as being associated with a particular stage of the particular brain disease. The prediction engine 260 can identify the regions of the brain, the brain disease, and the particular stage of the particular brain disease in the mental health prediction 262. In particular, if the prediction engine 260 can identify that the patient may have the particular brain disease in the mental health prediction 262 when the patient is still in an early stage of the particular brain disease, then the patient might be able to treat the particular brain disease in time before the particular brain disease enters a later stage.

As a particular example, Alzheimer's disease is known to be associated with parcellations that are in the frontal lobe of the brain during the mild cognitive impairment (MCI), and with parcellations that are in the parietal areas in later stages of the disease. As a particular example, a particular parcellation in the frontal lobe can have a high parcellation rank before the MCI stage (e.g., in the top ten of the parcellation ranking), and the parcellation rank can drop significantly during the MCI stage (e.g., drop by 100+ ranks in the parcellation ranking). If the particular parcellation and the typical change of its parcellation rank during the MCI stage is identified in the brain disease data 274, then the prediction engine 260 can identify that the patient may have Alzheimer's disease before the disease advances to later stages.

In some implementations, in addition to the centrality ranking data 252, the prediction engine 260 also processes network graph data, e.g., the network graph data 212 generated by the network graph generation system 210, to generate the mental health prediction 262. For example, the prediction engine 260 can use a number of brain tracts incident to each parcellation in the brain of the patient, a health of the tracts incident to each parcellation in the brain of the patient, or both to generate the mental health prediction 262.

In some implementations, the mental health prediction system 230 can process the centrality data 222 (and, optionally, the network graph data 212) using a machine learning model to generate the mental health prediction 262. The machine learning model has been trained to generate mental health predictions using training examples generated from the brain data of respective other patients and clinical outcomes of the other patients.

For example, the machine learning model can process a model input that includes a vector of centrality ranks, where each element of the vector identifies the centrality rank of a respective region of the brain of the patient. As a particular example, the machine learning model can be a deep neural network that is configured to process the model input to generate a model output that includes a prediction of whether the patient has a particular disease. For example, the model output can be a scalar value between 0 and 1 that characterizes a likelihood that the patient has the particular disease. As another particular example, the machine learning model can be a decision tree or a random forest that is configured to process the model input to generate a model output that includes a prediction of whether the patient has one or more particular diseases from a set of one or more diseases.

Figure 3:
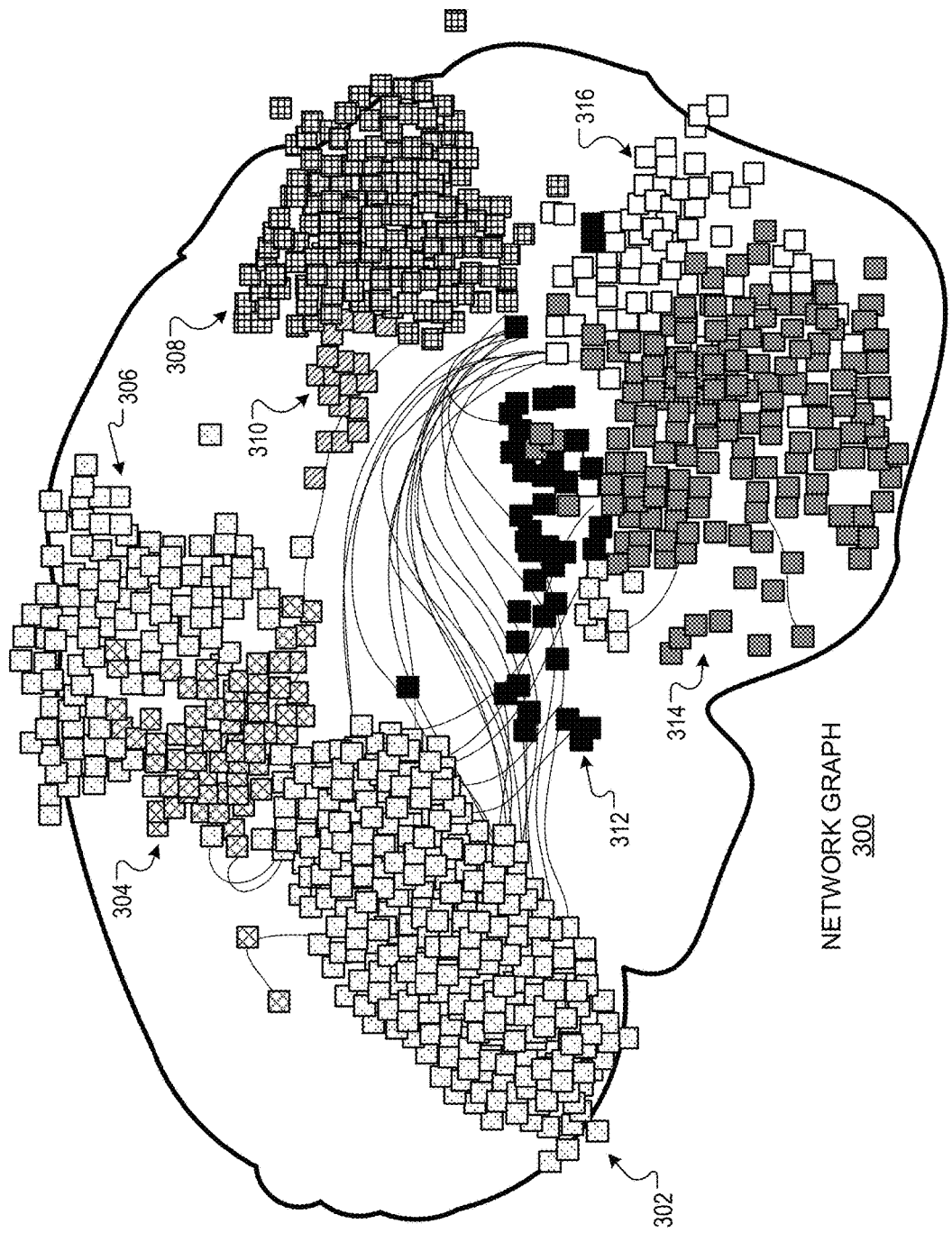
FIG. 3 illustrates a network graph characterizing the brain of a patient.

FIG. 3 illustrates an example network graph characterizing the brain of a patient.

Each node of the network graph corresponds to a respective parcellation in the brain of the patient. Each edge between a first node and a second node of the network graph corresponds to one or more brain tracts connecting the parcellation corresponding to the first node and the parcellation corresponding to the second node. Note that nodes and edges depicted in FIG. 3 are for illustrative purposes only; in reality, a network graph characterizing the brain of a patient can include many more nodes and edges, in many different configurations.

Generally, the edges of the network graph 300 are bidirectional; that is, the network graphs 300 is an undirected graph.

The network graph 300 includes eight subgraphs 302, 304, 306, 308, 310, 312, 314, and 316, depicted by respective different patterns. Each subgraph 302-316 corresponds to a respective functional area of the brain, and includes multiple parcellations.

In some implementations, the weights of the edges between respective nodes of the network graph 300 are machine-learned. For example, the weight for an edge between a first node and a second node can be a learned function of one or more of i) the number of tracts connecting the parcellation corresponding to the first node and the parcellation corresponding to the second node, or ii) a health of the tracts connecting the parcellation corresponding to the first node and the parcellation corresponding to the second node, e.g., according to fractional anisotropy data. For example, the weights can be a linear combination of those two terms. Instead of or in addition to those terms, the learned function can include a squared or cubed term corresponding to one or both of those two terms. As a particular example, if the machine learning model is a linear model, a training system can learn the parameters of the model using LASSO or ridge regression.

In some implementations, the weights of the edges of the network graph 300 can be learned concurrently with the weights of a machine learning model that is configured to generate a mental health prediction for the patient, e.g., a machine learning model in the prediction engine 260 depicted in FIG. 2B. That is, a training system can concurrently determine parameter updates to the weights of the edges of the network graph 300 and the parameters of the machine learning model.

In some implementations, the weights are the same for each edge in the network graph 300. In some other implementations, the weights for each edge in the network graph are different.

A brain data analysis system, e.g., the brain data analysis system 200 depicted in FIG. 2A, can determine a measure of centrality of each node in the network graph 300, e.g., determine the PageRank of each node. The brain data analysis system can then determine a centrality ranking of nodes in the network graph 300 according to the determined measures of centrality. The brain data analysis system can then use the determined centrality ranking to generate a mental health prediction for the patient.

Instead of or in addition, the brain analysis system can determine a centrality ranking for a single subgraph 302-316 of the network graph 300, and process the centrality ranking for the single subgraph to generate a mental health prediction for the user.

Figure 4:
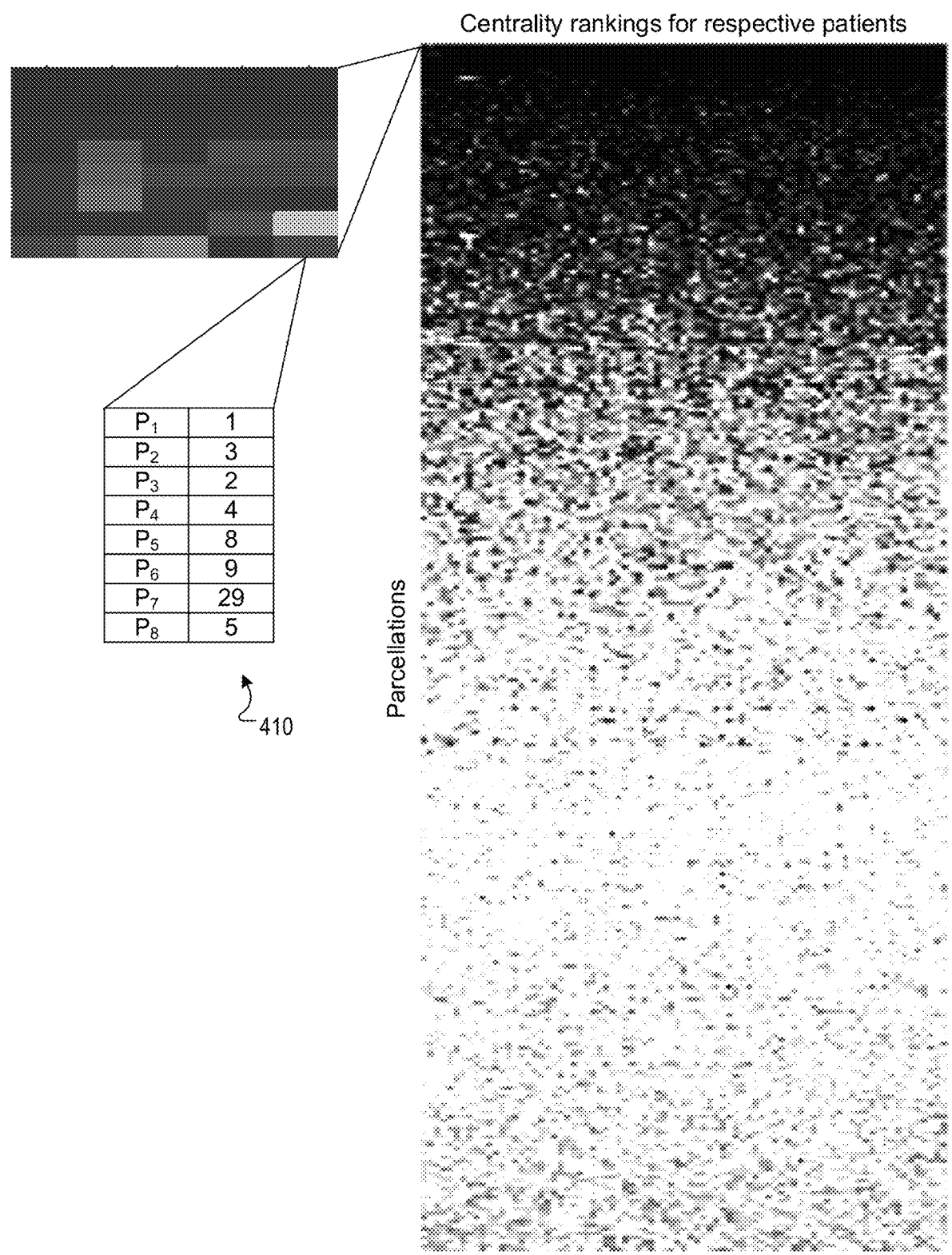
FIG. 4 illustrates example parcellation centrality rankings.

FIG. 4 illustrates example parcellation centrality rankings 400. Each column of the illustrated matrix corresponds to a respective centrality ranking 400, i.e., a centrality ranking 400 generated from brain data of a respective patient captured at a respective time.

Each row of the illustrated matrix corresponds to a particular parcellation in a set of parcellations. The rows are ordered according to the mean centrality rank of the corresponding parcellation according to the parcellation centrality rankings 400. The top row corresponds to the parcellation with the highest mean centrality rank (corresponding to the largest mean measure of centrality) and the bottom row corresponds to the parcellation with the lowest mean centrality rank (corresponding to the smallest mean measure of centrality).

The darkness (or, in other implementations, the color) of each element of the illustrated matrix characterizes the centrality rank of the parcellation corresponding to the row of the element in the centrality ranking 400 corresponding to the column of the element. A darker element indicates a higher centrality rank, while a lighter element indicates a lower centrality rank.

Thus, generally the darker elements in centrality rankings 400 (corresponding to higher centrality ranks) are in rows toward the top of the illustrated matrix, while the lighter elements in the centrality rankings 400 (corresponding to lower centrality ranks) are in rows toward the bottom of the illustrated matrix. Therefore, if there are lighter elements higher in the graph or darker elements lower in the graph, then this is an indication of a potential abnormal centrality ranking.

For example, there are examples where a darker element is in a row towards the bottom of the illustrated matrix. This indicates that the parcellation corresponding to the row typically has a relatively small measure of centrality (and thus a low centrality rank), but the parcellation has a relatively large measure of centrality in the brain data of the patient corresponding to the column (and thus a high centrality rank). If the parcellation is associated with a particular brain disease, then a mental health prediction system, e.g., the mental health prediction system 250 depicted in FIG. 2B, might identify the parcellation in a mental health prediction for the patient. For example, the particular brain disease might be associated with an unusually high centrality rank for the parcellation.

Further, there are examples where a lighter element is in a row towards the top of the illustrated matrix. This indicates that the parcellation corresponding to the row typically has a relatively large measure of centrality (and thus a high centrality rank), but the parcellation has a relatively small measure of centrality in the brain data of the patient corresponding to the column (and thus a low centrality rank). If the parcellation is associated with a particular brain disease, then a mental health prediction system might identify the parcellation in a mental health prediction for the patient. For example, the particular brain disease might be associated with an unusually low centrality rank for the parcellation.

As an illustrative example, the eight parcellations (labeled $P_1$-$P_8$) with the highest mean centrality rank in the set of parcellations are illustrated in FIG. 4, along with, for each of the eight parcellations $P_1$-$P_8$, the respective centrality rank of the parcellation in a particular centrality ranking 410 corresponding to a particular patient.

That is, the parcellation $P_1$ has the highest mean centrality rank in the set of parcellations, and has the highest centrality rank in the particular centrality ranking 410. The parcellation $P_2$ has the second highest mean centrality rank in the set of parcellations, and the third highest centrality rank in the particular centrality ranking 410. The parcellation $P_3$ has the third highest mean centrality rank in the set of parcellations, and the second highest centrality rank in the particular centrality ranking 410, and so on.

A mental health prediction system, e.g., the mental health prediction system 250 depicted in FIG. 2B, can obtain the particular centrality ranking 410 and process the particular centrality ranking to generate a mental health prediction for the particular patient. For example, the mental health prediction system can obtain normal centrality ranking data, e.g., data that characterizes the mean centrality rank for each parcellation in the set of parcellations, and compare the particular centrality ranking 410 against the normal centrality ranking data to generate the mental health prediction.

As a particular example, the mental health prediction system can identify that parcellation $P_7$ has the seventh highest mean centrality rank in the set of parcellation, and yet has the $29^{th}$ highest centrality rank in the particular centrality ranking 410. Because the difference between the mean centrality rank of parcellation $P_7$ and the actual centrality rank of parcellation $P_7$ in the particular centrality ranking 410 is so large (e.g., larger than a threshold of 10 or 20 positions), the mental health prediction system can identify the parcellation $P_7$ in the generated mental health prediction. The mental health prediction system can also identify one or more diseases associated with the parcellation $P_7$, e.g., one or more diseases associated with a centrality rank drop of more than 20 positions for the parcellation $P_7$.

Figure 5:
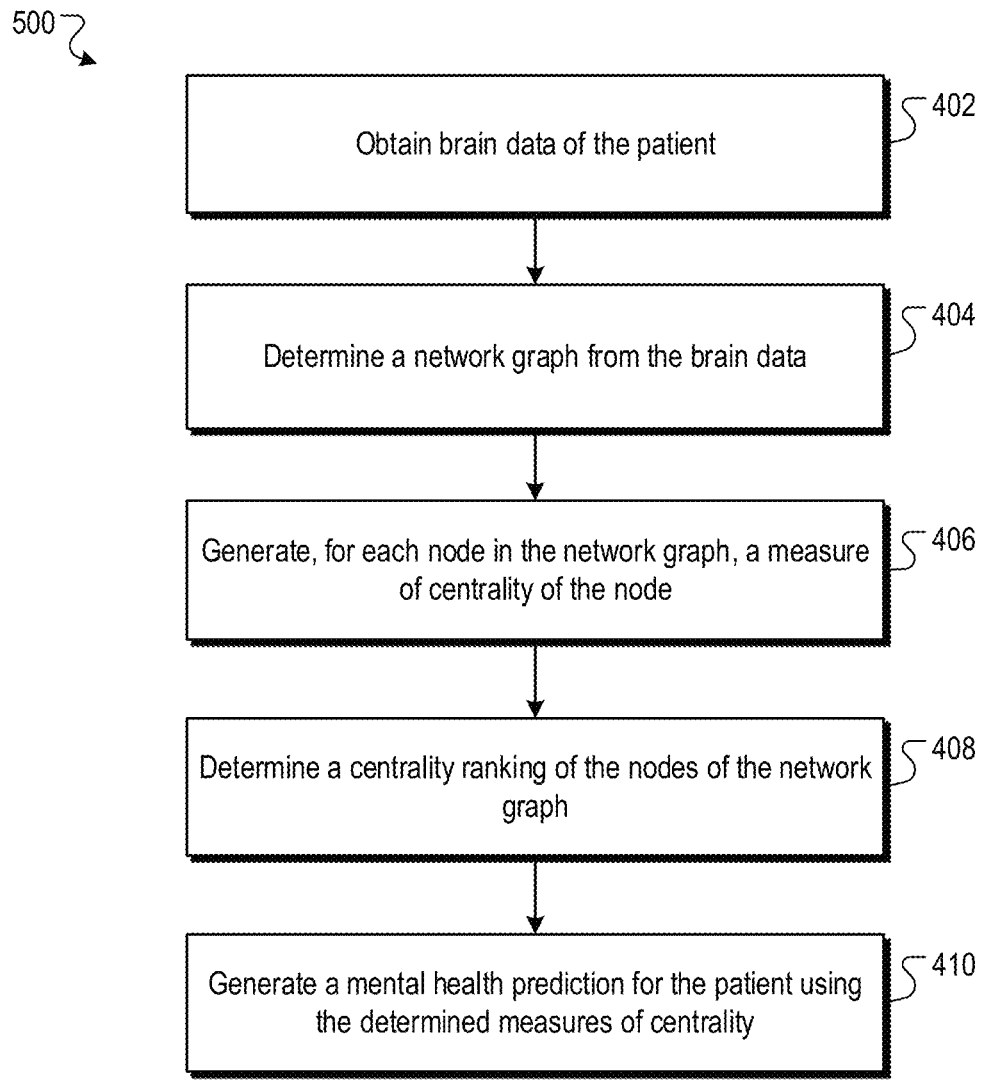
FIG. 5 is a flowchart of an example process for generating a mental health prediction for a patient using a centrality ranking generated from brain data of the patient.

FIG. 5 is a flowchart of an example process 500 for generating a mental health prediction for a patient using a centrality ranking generated from brain data of the patient. The process 500 can be implemented by one or more computer programs installed on one or more computers and programmed in accordance with this specification. For example, the process 500 can be performed by the computer server module depicted in FIG. 1A. For convenience, the process 500 will be described as being performed by a system of one or more computers.

The system obtains brain data of the patient (step 502). The brain data can be captured by one or more sensors. The brain data can include, for each of multiple pairs of parcellations formed from a set of parcellations where each pair includes a first parcellation and a second parcellation, data characterizing the number of tracts connecting the first parcellation and the second parcellation.

The system determines a network graph from the brain data of the patient (step 504). One or more nodes of the network graph can correspond to a parcellation in the brain of the patient. A subset of the nodes can correspond to the particular region of the brain of the patient, e.g., a particular functional area such as can be determined by a brain atlas (e.g., the MNI atlas). One or more edges between a first node and a second node of the network graph can characterize a connection between the parcellation corresponding to the first node and the parcellation corresponding to the second node.

In some implementations, the system generates an edge weight for each edge in the network graph. For example, the system can generate the edge weight according to the number of tracts between the parcellations corresponding to the respective nodes and/or a measure of health of the tracts between the parcellations corresponding to the respective nodes. For example, the edge weight can be a learned linear combination of the number of tracts and the measure of health of the tracts.

The system generates a measure of centrality for each node in the network graph (step 506). For example, the system can determine the PageRank of each node in the network graph. In some implementations, the system only generates a measure of centrality for nodes in the network graph that correspond to parcellations that are in the particular region of the brain.

The system determines a centrality ranking of the nodes in the network graph according the determined measures of centrality (step 508). That is, the system can determine, for each node, a centrality rank for the node among all nodes of the network graph according to its respective measure of centrality.

In some implementations, determining a centrality ranking for the brain of the patient can require extensive computation, e.g., when there are hundreds, thousands, or millions of machine-learned parameters to compute. As a particular example, the process 500 can take multiple hours for a computer system to perform.

The system generates a mental health prediction for the patient using the determined centrality rankings (step 510).

The mental health prediction can include an identification of one or more parcellations in the brain of the patient whose centrality ranks were determined by the system to be abnormal. For example, the system can obtain "normal" centrality ranking data that identifies, for each parcellation in the brain of the patient, a range of normal centrality rankings. The system can then determine one or more parcellations whose centrality ranks in the generated centrality ranking of the patient are outside of the range of normal centrality ranks.

The mental health prediction can include a recommendation to consider performing a particular treatment for the brain of the patient. For example, the particular treatment can be associated with a particular centrality rank or range of centrality ranks of one or more parcellations of the brain. That is, the system can use previous clinical outcomes and corresponding centrality rankings of other patients to determine the range of centrality ranks of the one or more parcellations. The range of centrality ranks defines centrality ranks of the parcellations that patients have had when the patients have achieved the most clinical success with the particular treatment. For example, the system can use a machine learning model that has been trained using training examples corresponding to respective patients with specified clinical outcomes to determine the range of centrality ranks of the one or more parcellations.

Similarly, the particular treatment can be associated with a range of changes of centrality ranks of the one or more parcellations across time. That is, the system can use previous clinical outcomes and corresponding changes in the centrality rankings of other patients across time to determine the range of changes of centrality ranks of the one or more parcellations. The range of changes of centrality ranks defines changes in the centrality ranks of the parcellations that patients have experienced before the patients achieved the most clinical success with the particular treatment. For example, the system can use a machine learning model that has been trained using training example corresponding to respective patients to determine the range of changes of centrality ranks of the one or more parcellations.

As a particular example, a patient might have a tumor in the particular region of the brain, and a clinician may be attempting to select a treatment plan. Using the centrality rank of one or more parcellations in the particular region, the clinician can better determine whether or not the particular region would react well to surgery. For example, the centrality ranks of the one or more parcellations might be too low, indicating that the particular region is already significantly deteriorated. In this case surgery might be too dangerous to the particular region of the brain, or the particular region of the brain might be unsalvageable making surgery an unnecessary risk to the patient. The thresholds of the centrality ranks of the one or more parcellations for determining whether to perform surgery can be determined over time using the data and clinical outcomes of multiple different patients.

Instead or in addition, the mental health prediction can include a prediction of whether the patient has a particular brain disease. For example, the brain disease can be associated with a range of centrality ranks of one or more parcellations in a particular region of the brain. That is, the system can use previous diagnoses and corresponding centrality rankings of other patients to determine the range of centrality ranks of the one or more parcellations. That range of centrality ranks defines centrality ranks of the one or more parcellations of a group of patients who are known to have the particular brain disease. For example, the system can use a machine learning model that has been trained using training examples corresponding to respective patients to determine the range of centrality ranks of the one or more parcellations.

Similarly, the brain disease can be associated with a range of changes of centrality ranks of the one or more parcellations across time. That is, the system can use previous clinical outcomes and corresponding changes in the centrality rankings of other patients across time to determine the range of changes of centrality ranks of the one or more parcellations. The range of changes of centrality ranks defines changes in the centrality ranks of the parcellations that a group of patient who are known to have the brain disease experienced. For example, the system can use a machine learning model that has been trained using training example corresponding to respective patients to determine the range of changes of centrality ranks of the one or more parcellations.

As a particular example, Alzheimer's often causes the brain to atrophy asymmetrically, i.e., some regions of the brain atrophy more quickly than others. For example, the "default mode" network of the brain is known to atrophy quickly in Alzheimer's patients. Using the process 400, the system can generate a centrality rank for each parcellation in the default mode network for a patient who has been diagnosed with Alzheimer's, e.g., in order to determine the stage of the disease. The system can also generate centrality ranks for the default mode network for a patient who is suspected of having Alzheimer's, in order to diagnose the disease. In either case, the thresholds of the centrality ranks of the parcellations in the default mode network for determining the stage of the disease can be determined over time using the data and clinical outcomes of multiple different patients Instead or in addition, the mental health prediction can include a prediction of how the brain of the patient is changing over time. For example, the system can generate multiple centrality rankings corresponding to respective time points using the process 400, and determine a change between the respective centrality rankings.

For example, the system can determine one or more parcellations whose centrality ranks have changed over time across the multiple generated centrality rankings. One or more diseases can be associated with the determined parcellations, and the system can identify the one or more diseases in the mental health prediction. As a particular example, a disease may be associated with a particular magnitude of the change of the centrality ranks of the one or more parcellations, e.g., a respective number of positions in the centrality ranking that each parcellation has changed.

As another example, the system can generate a respective centrality ranking for the brain of the patient before and after a treatment. The treatment can include one or more of: a drug therapy, radiation therapy, magnetic therapy (e.g., TMS), light therapy (e.g., laser ablation), ultrasonic therapy (e.g., ablation), gene-modifying therapy, a surgery, physical therapy, yoga, or mental exercises, e.g., mental games or puzzles. The system can then determine a difference between the multiple centrality rankings and generate the mental health prediction using the determined difference.

As a particular example, the mental health prediction can include a measure of efficacy of the treatment that was administered to the brain of the patient. That is, the system can i) process brain data captured before the treatment to generate a first centrality ranking and ii) process brain data captured after the treatment to generate a second centrality ranking. The system can then determine, according to the respective centrality rankings, how effective the treatment was, e.g., whether one or more particular parcellations had an abnormal centrality rank before the therapy and a normal centrality rank after the therapy. Instead or in addition, the mental health prediction can include a performance measure for one or more entities that administered the treatment. That is, the system can determine, according to the respective centrality rankings, how well the one or more entities administered the treatment. For example, the one or more entities can include one or more clinicians and/or one or more medical devices.

Instead or in addition, the mental health prediction can include a plan to administer a sequence of one or more treatments to the patient. For example, the system can determine (e.g., automatically or with the approval of a clinician) to administer a first treatment until a first benchmark is achieved, a second treatment until a second benchmark is achieved, etc. Each benchmark can correspond to a particular centrality rank of one or more parcellations in the brain of the patient. That is, during the sequence of treatments the system can iteratively generate centrality rankings of the brain of the patient using the process 400, and whenever a benchmark is achieved the system can instruct a change to, or recommend that a user change, the treatment of the patient.

Instead or in addition, the mental health prediction can include a prediction of a relationship between different regions of the brain over time. For example, the system can use the process 400 to determine a respective centrality ranking of the brain of the patient at a first time point, and then determine a respective centrality ranking of the brain of the patient at a second, later time point. The system can then determine how the centrality ranks of one or more parcellations in a first region of the brain are changing in relation to the centrality ranks of one or more parcellations in a second region of the brain are changing. The system can use this information, e.g., to recommend treatment, to schedule follow-up tests for the patient, and/or to categorize the patient.

In some implementations, the system can perform the process 500 continuously in real-time. That is, the system can iteratively obtain new brain data of a patient and process the brain data to generate a new mental health prediction for the patient.

As a particular example, while a patient is undergoing brain surgery, the system can continuously capture brain data of the patient (e.g., using intraoperative MM), and process the brain data to determine if further resection is feasible without causing neurological deficit. For example, the system can determine whether the centrality ranks of one or more parcellations affected by the surgery have decreased.

As another particular example, a clinician or the system can apply an electrical current to a particular region of the brain of a patient through an implantable stimulator and determine one or more changes in the centrality ranks of respective parcellations in the particular region of the brain across time. For example, the system can generate a mental health prediction, using a change in the centrality ranks of the parcellations in the particular region of the brain, that indicates whether the electrical current is being properly placed and/or whether the parameters are properly designed. The mental health prediction can also identify how the placement of the electrical current and/or the parameters of the electrical current might be adjusted.

As another particular example, before administering a therapy to a patient (e.g., before administering a drug), a clinician can perform subtherapeutic tests of the therapy, where the therapy is delivered at a lower rate than is typically deemed therapeutic. The system can receive brain data of the patient that was captured during or after the subtherapeutic tests, and process the brain data to generate a mental health prediction that includes a prediction of the efficacy of the therapy, prior to the administration of the therapy. Instead or in addition, the mental health prediction can identify one or more side effects of the therapy, prior to the administration of the therapy.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g, a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return. Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:
  obtaining brain data captured by one or more sensors characterizing a brain of a patient, wherein the brain data comprises, for each of a plurality of pairs of parcellations formed from a set of parcellations where each pair comprises a first parcellation and a second parcellation, data characterizing a number of tracts connecting the first parcellation and the second parcellation;
  determining a network graph from the brain data, wherein a node of the network graph corresponds to a parcellation in the brain of the patient;
  generating, for each of a plurality of nodes in the network graph, a measure of centrality of the node;
  determining a centrality ranking of the plurality of nodes of the network graph according to the respective measures of centrality;
  generating a mental health prediction for the patient using the determined centrality ranking.

Embodiment 2 is the method of embodiment 1, wherein:
  an edge between a first node and a second node of the network graph characterizes a connection between the parcellation corresponding to the first node and the parcellation corresponding to the second node, and
  determining a network graph from the brain data comprises, for an edge between a first node and a second node of the network graph, generating an edge weight according to the number of tracts connecting the parcellation corresponding to the first node and the parcellation corresponding to the second node.

Embodiment 3 is the method of any one of embodiments 1 or 2, wherein:
  the brain data was captured at a first time point and the centrality ranking is a first centrality ranking;
  the method further comprises obtaining second brain data captured at a second time point and processing the second brain data to generate a second centrality ranking; and
  generating a mental health prediction for the patient comprises:
    determining a difference between the first centrality ranking and the second centrality ranking; and
    generating the mental health prediction using the determined difference.

Embodiment 4 is the method of embodiment 3, wherein:
  the first time point is a time point before a treatment, and the second time point is a time point after the treatment.

Embodiment 5 is the method of embodiment 4, wherein the treatment comprises one or more of:
  a drug therapy;
  radiation therapy;
  magnetic therapy;
  light therapy;
  ultrasonic therapy;
  gene-modifying therapy;
  a surgery;
  physical therapy; or
  mental exercises.

Embodiment 6 is the method of any one of embodiments 3-5, wherein:
  determining a difference between the first centrality ranking and the second centrality ranking comprises determining one or more first parcellations whose corresponding node has a different rank in the first centrality ranking than in the second centrality ranking; and
  generating the mental health prediction using the determined difference comprises identifying a disease associated with the one or more first parcellations.

Embodiment 7 is the method of embodiment 6, wherein:
  the determined difference, for one or more of the first parcellations, comprises a determined magnitude of the difference between the rank of the first parcellation in the first centrality ranking and the rank of the first parcellation in the second centrality ranking, and
  the identified disease is associated with the determined magnitude of the difference.

Embodiment 8 is the method of any one of embodiments 3-7, wherein the mental health prediction comprises one or more of:
  a measure of efficacy of the treatment; or
  a performance measure of one or more entities that administered the treatment.

Embodiment 9 is the method of any one of embodiments 1-8, wherein generating a mental health prediction for the patient comprises:
  obtaining ranking data characterizing, for each node in the network graph, a normal rank of the node in a centrality ranking of the nodes, wherein the ranking data has been generated using brain data corresponding to a plurality of second patients;
  determining, for one or more first parcellations, a difference between i) the rank of the node corresponding to the first parcellation in the determined centrality ranking of the nodes, and ii) the normal rank for the node corresponding to the first parcellation characterized by the obtained ranking data; and generating the mental health prediction using the determined difference.

Embodiment 10 is the method of any one of embodiments 1-9, wherein:

each node of a plurality of nodes of the network graph corresponds to a parcellation in the brain of the patient, and each edge of a plurality of edges between a respective first node and second node of the network graph characterizes a connection between the parcellation corresponding to the first node and the parcellation corresponding to the second node.

Embodiment 11 is the method of any one of embodiments 1-10, wherein generating a mental health prediction for the patient comprises determining whether to perform a particular treatment on the brain of the patient.

Embodiment 12 is the method of embodiment 11, wherein the particular treatment is associated with i) a range of centrality rankings of a particular parcellation, ii) a range of changes in centrality rankings across time of a particular parcellation, or iii) both.

Embodiment 13 is the method of embodiment 12, wherein one or more of the ranges is machine learned, the learning comprising processing a plurality of training examples corresponding to respective other patients.

Embodiment 14 is the method of any one of embodiments 1-13, wherein generating a mental health prediction for the patient comprises generating a prediction of whether the patient has a particular brain disease.

Embodiment 15 is the method of embodiment 14, wherein the particular brain disease is associated with i) a range of centrality rankings of a particular parcellation, ii) a range of changes in centrality rankings across time of a particular parcellation, or iii) both.

Embodiment 16 is the method of embodiment 15, wherein one or more of the ranges is machine learned, the learning comprising processing a plurality of training examples corresponding to respective other patients.

Embodiment 17 is a system comprising one or more computers and one or more storage devices storing instructions that are operable, when executed by the one or more computers, to cause the one or more computers to perform the method of any one of embodiments 1-16.

Embodiment 18 is a computer storage medium encoded with a computer program, the program comprising instructions that are operable, when executed by data processing apparatus, to cause the data processing apparatus to perform the method of any one of embodiments 1-16.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:

1. A method comprising:

obtaining, by one or more processing devices, brain data captured by one or more brain sensing devices characterizing a brain of a patient, wherein the brain data comprises, for each of a plurality of pairs of parcellations formed from a set of parcellations in the brain of the patient, data characterizing a connectivity between the pair of parcellations, the set of parcellations comprising at least 100 parcellations;

generating, by the one or more processing devices and from the brain data, data representing a network graph comprising a plurality of nodes, wherein one or more nodes of the plurality of nodes of the network graph correspond to respective parcellations in the brain of the patient;

generating, for at least a subset of the plurality of nodes in the network graph, a measure of centrality of the node;

determining a centrality ranking of at least the subset of the plurality of nodes of the network graph according to the respective measures of centrality;

generating a mental health prediction for the patient using the determined centrality ranking; and providing, for display on a user device, data characterizing the mental health prediction.

2. The method of claim 1, wherein:

at least a second subset of the plurality of nodes of the network graph corresponds to a particular functional area of the brain, the particular functional area of the brain comprising a plurality of parcellations from the set of parcellations, and generating the measures of centrality comprises generating a measure of centrality for each node in the second subset.

3. The method of claim 1, wherein:

an edge between a first node and a second node of the network graph characterizes a connection between a parcellation corresponding to the first node and a parcellation corresponding to the second node, and determining a network graph from the brain data comprises, for the edge between the first node and the second node of the network graph, generating an edge weight according to the connectivity, identified from the brain data, between the parcellation corresponding to the first node and the parcellation corresponding to the second node.

4. The method of claim 3, wherein the edge weight for the edge between the first node and the second node in the network graph is generated according to one or more of i) a number of tracts connecting the parcellation corresponding to the first node and the parcellation corresponding to the second node, or ii) a measure of health of the tracts connecting the parcellation corresponding to the first node and the parcellation corresponding to the second node.

5. The method of claim 4, wherein the edge weight for the edge between the first node and the second node is a machine-learned combination of i) the number of tracts connecting the parcellation corresponding to the first node and the parcellation corresponding to the second node and ii) the measure of health of the tracts connecting the parcellation corresponding to the first node and the parcellation corresponding to the second node.

6. The method of claim 1, wherein:
the brain data was captured at a first time point and the centrality ranking is a first centrality ranking;
the method further comprises obtaining second brain data captured at a second time point and processing the second brain data to generate a second centrality ranking; and
generating a mental health prediction for the patient comprises:
determining a difference between the first centrality ranking and the second centrality ranking; and
generating the mental health prediction using the determined difference.

7. The method of claim 6, wherein:
the first time point is a time point before a treatment was provided to the patient, and
the second time point is a time point after the treatment was provided to the patient.

8. The method of claim 7, wherein generating the mental health prediction comprises one or more of:
generating a measure of efficacy of the treatment; or
generating a performance measure of one or more entities that administered the treatment.

9. The method of claim 7, wherein the treatment provided to the patient included one or more of:
a drug therapy;
radiation therapy;
magnetic therapy;
light therapy;
ultrasonic therapy;
gene-modifying therapy;
a surgery;
physical therapy; or
mental exercises.

10. The method of claim 6, wherein:
determining a difference between the first centrality ranking and the second centrality ranking comprises determining one or more first parcellations whose corresponding node in the network graph has a different rank in the first centrality ranking than in the second centrality ranking; and
generating the mental health prediction using the determined difference comprises identifying a disease associated with the one or more first parcellations.

11. The method of claim 10, wherein:
the determined difference, for one or more of the first parcellations, comprises a determined magnitude of the difference between the rank of the first parcellation in the first centrality ranking and the rank of the first parcellation in the second centrality ranking, and
the identified disease is associated with the determined magnitude of the difference.

12. The method of claim 1, wherein generating a mental health prediction for the patient comprises:
obtaining ranking data characterizing, for at least the subset of the plurality of nodes in the network graph, a normal rank of the node in a centrality ranking of the nodes, wherein the ranking data has been generated using brain data corresponding to a plurality of second patients;
determining, for one or more first parcellations, a difference between i) a rank of the node corresponding to the first parcellation in the determined centrality ranking of the nodes, and ii) the normal rank for the node corresponding to the first parcellation characterized by the obtained ranking data; and
generating the mental health prediction using the respective determined difference for the one or more first parcellations.

13. The method of claim 1, wherein:
each node of the plurality of nodes of the network graph corresponds to a respective parcellation in the brain of the patient, and
each edge of a plurality of edges between a respective first node and second node of the network graph characterizes a connection between the parcellation corresponding to the first node and the parcellation corresponding to the second node.

14. The method of claim 1, wherein generating a mental health prediction for the patient comprises determining a recommended treatment to provide to the patient.

15. The method of claim 14, wherein the recommended treatment is associated with, for each of one or more particular parcellations, i) a range of ranks of the particular parcellation in the centrality ranking, ii) a range of changes in ranks across time of the particular parcellation, or iii) both.

16. The method of claim 15, wherein one or more of the ranges is machine-learned, the learning comprising processing a plurality of training examples corresponding to respective other patients.

17. The method of claim 1, wherein generating a mental health prediction for the patient comprises generating a prediction of whether the patient has a particular brain disease.

18. The method of claim 17, wherein the particular brain disease is associated with, for each of one or more particular parcellations, i) a range of ranks of the particular parcellation in the centrality ranking, ii) a range of changes in ranks across time of the particular parcellation, or iii) both.

19. The method of claim 18, wherein one or more of the ranges is machine-learned, the learning comprising processing a plurality of training examples corresponding to respective other patients.

20. A system comprising one or more computers and one or more storage devices storing instructions that are operable, when executed by the one or more computers, to cause the one or more computers to perform operations comprising:
obtaining, by one or more processing devices, brain data captured by one or more brain sensing devices characterizing a brain of a patient, wherein the brain data comprises, for each of a plurality of pairs of parcellations formed from a set of parcellations in the brain of the patient, data characterizing a connectivity between the pair of parcellations, the set of parcellations comprising at least 100 parcellations;

generating, by the one or more processing devices and from the brain data, data representing a network graph comprising a plurality of nodes, wherein one or more nodes of the plurality of nodes of the network graph correspond to respective parcellations in the brain of the patient;

generating, for at least a subset of the plurality of nodes in the network graph, a measure of centrality of the node;

determining a centrality ranking of at least the subset of the plurality of nodes of the network graph according to the respective measures of centrality;

generating a mental health prediction for the patient using the determined centrality ranking; and providing, for display on a user device, data characterizing the mental health prediction.

21. One or more non-transitory computer storage media encoded with computer program instructions that when executed by a plurality of computers cause the plurality of computers to perform operations comprising:

obtaining, by one or more processing devices, brain data captured by one or more brain sensing devices characterizing a brain of a patient, wherein the brain data comprises, for each of a plurality of pairs of parcellations formed from a set of parcellations in the brain of the patient, data characterizing a connectivity between the pair of parcellations, the set of parcellations comprising at least 100 parcellations;

generating, by the one or more processing devices and from the brain data, data representing a network graph comprising a plurality of nodes, wherein one or more nodes of the plurality of nodes of the network graph correspond to respective parcellations in the brain of the patient;

generating, for at least a subset of the plurality of nodes in the network graph, a measure of centrality of the node;

determining a centrality ranking of at least the subset of the plurality of nodes of the network graph according to the respective measures of centrality;

generating a mental health prediction for the patient using the determined centrality ranking; and providing, for display on a user device, data characterizing the mental health prediction.

* * * * *